United States Patent [19]

Schäfer

[11] Patent Number: 4,945,180

[45] Date of Patent: Jul. 31, 1990

[54] PROCESS FOR THE PREPARATION OF E-2-PROPYL-2-PENTENOIC ACID AND PHYSIOLOGICALLY COMPATIBLE SALTS THEREOF

[75] Inventor: Helmut Schäfer, Kayhyde, Fed. Rep. of Germany

[73] Assignee: Desitin Arzneimittel GmbH, Hamburg, Fed. Rep. of Germany

[21] Appl. No.: 203,291

[22] Filed: Jun. 2, 1988

[30] Foreign Application Priority Data

Jun. 2, 1987 [DE] Fed. Rep. of Germany ....... 3718803

[51] Int. Cl.$^5$ ................... C07C 51/377; C07C 51/41; C07C 51/08; C07C 57/03
[52] U.S. Cl. ..................................... 562/599; 562/579; 562/598; 562/600; 558/462
[58] Field of Search .......................... 562/599, 579, 598

[56] References Cited

U.S. PATENT DOCUMENTS 4,127,604 11/1978 Chignac et al. ..................... 562/606

FOREIGN PATENT DOCUMENTS 1195295 6/1965 Fed. Rep. of Germany ...... 562/599

Primary Examiner—Vivian Garner
Attorney, Agent, or Firm—Nixon & Vanderhye

[57] ABSTRACT

A novel process for the preparation of E-2-propyl-2-pentenoic acid and its physiologically compatible salts is described, in which di-n-propyl-ketone-cyanohydrin is used as the starting compound. The compound is either (a) dehydrated with thionyl chloride and the acid nitrile formed is subsequently saponified with a stoichiometric excess of potassium hydroxide, or (b) is initially converted into 2-hydroxy-2-propyl-pentanoic acid and the latter is subsequently dehydrated in the presence of a less than stoichiometric quantity of a tertiary amine at a temperature of at least 200° C.

The free acid is optionally converted into the salt form, preferably using the corresponding salts of carbon dioxide in an aqueous acetone solution.

7 Claims, No Drawings

PROCESS FOR THE PREPARATION OF E-2-PROPYL-2-PENTENOIC ACID AND PHYSIOLOGICALLY COMPATIBLE SALTS THEREOF

DESCRIPTION

E-2-propyl-2-pentenoic acid, a derivative of valproic acid, has of late awakened considerable interest as a possible therapeutic for the treatment of epilepsy. Thus, whereas in the case of a conventional treatment with valproic acid heptotoxic and teratogenic characteristics are to be feared in certain cases, comparative animal tests with E-2-propyl-2-pentenoic acid reveal that, with an at least equivalent therapeutic activity, it leads to no heptotoxic or teratogenic effects (cf. W. Loscher, Drugs of the Future, 10, 389–391, 1985). The toxicologically favourable characteristics are particularly observed in the case of the E-isomer of 2-propyl-2-pentenoic acid.

E-2-propyl-2-pentenoic acid is a crystalline compound with a melting point of 38° to 40° C. and which has long been known as such, having the formula I

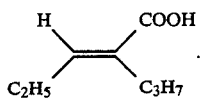

The preparation of 2-propyl-2-pentenoic acid from the 4-heptanone cyanohydrin of Formula II

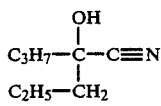

is already known.

By reacting the compound of Formula II with concentrated sulphuric acid, it is firstly possible to prepare the corresponding acid amide and then the acid. However, in this process, apart from further decomposition and rearrangement products, mainly the Z-isomer of the desired acid is formed.

The problem of the present invention is consequently to provide a process in which the formation of the E-isomer of 2-propyl-2-pentenoic acid is favoured.

According to the invention, it has surprisingly been found that on the basis of Formula II in preferred manner the E-isomer of 2-propyl-2-pentenoic acid is obtained if either (a) the starting compound is dehydrated with thionyl chloride and subsequently the acid nitrile of formula III

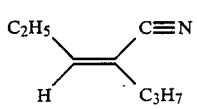

mainly formed as Z-isomer is saponified with a stoichiometric excess of potassium hydroxide in glycerol at temperatures of at least 130° C., or (b) the starting compound is initially converted in known manner into 2-hydroxy-2-propyl pentanoic acid of the formula IV

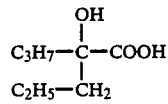

and the latter is subsequently dehydrated in the presence of a substroichiometric quantity of a tertiary amine, preferably N-methyl-pyrrolidine, at a temperature of at least 200° C.

The literature (cf. Houben-Weyl) has already referred to the possibility of saponifying nitriles with the aid of dilute KOH solutions in glycerol at temperatures above 150° C. However, it was not to be expected that in the case of the inventively used high KOH concentrations in glycerol and after boiling for several hours a crude product would be obtained, of which more than 60% consists of the E-isomer of the desired acid. The reaction of the starting compound according to Formula II with thionyl chloride initially mainly supplies the Z-isomer of the compound according to Formula III. This reaction is performed at 70° to 100° C. and preferably at 80° to 90° C. for 2 to 4 hours under reflux. The thionyl chloride is preferably used in a quantity such that it is sufficient for dissolving the starting compound and for obtaining the indicated reflux temperature.

The reaction mixture is subsequently mixed with water in order to remove excess thionyl chloride. The organic phase is then separated using e.g. methyl-tert-butyl ether. The combined organic phases are subsequently washed and distilled in order to extract 2-propyl-2-pentene nitrile mainly as Z-isomer. In the following process stage a solution of KOH in glycerol is firstly prepared by slow heating and the acid nitrile is subsequently added dropwise. The inventively used KOH quantity is above the stoichiometric quantity and the equivalence ratio of potassium hydroxide to acid nitrile in the mixture is preferably 3:1 to 4.5:1.

The reaction mixture is subsequently refluxed for 6 to 10 and preferably 8 hours, a temperature of at least 130° C., but preferably 140° to 150° C. being reached. At the end of the reaction time the mixture is acidified e.g. with concentrated hydrochloric acid and the separating oil phase is taken up in an organic solvent, such as e.g. n-hexane. After washing the organic phase a crude product is obtained by evaporation and which contains in preferred manner the E-isomer of 2-propyl-2-pentenoic acid. This can be separated from the crude product by precision distillation.

As explained hereinbefore the starting compound according to Formula II can be initially converted into 2-hydroxy-2-propyl pentanoic acid and subsequently dehydrated to obtain the desired end product according to the invention.

Thermal dehydration of 2-hydroxy-2-propyl pentanoic acid is also known. However, according to the known process, the reaction product obtained mainly consists of the Z-isomer. It has surprisingly been found according to the invention that through the addition of less than the stoichiometric quantity of a tertiary amine, thermal dehydration from 2-hydroxy-2-propyl pentanoic acid preferably leads to the formation of the E-isomer of the en-acid.

The 2-hydroxy-2-propyl pentanoic acid can be obtained from the starting compound of Formula II, e.g. by saponifying with concentrated hydrochloric acid.

The acid is subsequently heated with a tertiary amine, preferably N-methyl-pyrrolidine to a temperature above 200° C. The amine quantity used is preferably 5 to 10 mole %, based on the starting compound of Formula II and the reaction is performed for approximately 1 hour at a temperature of 200° to 250° C., preferably 230° to 240° C. It is ended after approximately 1 hour. Here again, the oily residue is taken up by acidification in an organic solvent, such as e.g. n-hexane, washed with dilute mineral acid and subsequently distilled.

If desired, the free acid can be converted in the conventional manner into the form of a physiologically compatible salt.

According to a particularly preferred embodiment the reaction is performed in aqueous acetone as the solvent in the presence of the corresponding salt of carbon dioxide. If, e.g., the sodium salt of E-2-propyl-2-pentenoic acid is to be prepared, then preferably sodium carbonate in a solution of the free acid is refluxed for a few hours in an acetone/water mixture. After cooling to a temperature below 0° C., the sodium salt is obtained as a precipitate of fine white crystals.

The invention will now be illustrated by means of the following examples.

EXAMPLE 1

Preparation of 2-propyl-2-pentene nitrile 535 g of thionyl chloride are placed in a two liter flask. At an internal temperature of 30° to 35° C., 353 g of di-n-propyl-ketone-cyanohydrin are added dropwise over 3 hours. The reaction mixture is then heated for 3 hours under slight reflux to 80° to 90° C., the gases HCl and $SO_2$ escaping via the reflux condenser being absorbed by a 40% caustic soda solution. The reaction mixture is then stirred with 390 ml of water for decomposing excess thionyl chloride. After separating the organic phases, the aqueous phase is washed with 200 ml of methyl-tert-butyl ether. The combined organic phases are distilled over a column following washing with 10% caustic soda solution and water.

The yield is 254 g, corresponding to 82.5% of theory; b.p.$_{17}$: 62°–64° C.

The 2-propyl-2-pentene nitrile obtained in this way is a mixture of Z and E-isomers in a ratio of approximately 80:20.

EXAMPLE 2

Preparation of E-2-propyl-2-pentenoic acid from 2-propyl-2-pentene nitrile (Z/E ratio approximately 80:20)

1425 g of glycerol are placed in a four liter flask. 470 g of KOH are added and the mixture is slowly heated, the potassium hydroxide dissolving at approximately 100° C. After reaching a temperature of 140° C., over a period of 1½ hours 264.4 g of 2-propyl-2-pentene nitrile are added dropwise, the temperature being kept at 140° to 145° C. Slight foaming initially occurs. The reaction mixture is refluxed for 8 hours, accompanied by the escape of ammonia and followed by mixing with 1700 ml of water. After cooling a roughly 2 cm thick, flaky foam layer has deposited on the clear yellow solution. The reaction mixture is acidified to pH 1 with 620 ml of concentrated hydrochloric acid. The separated oil is then taken up with 100 ml of n-hexane and the aqueous phase is again extracted twice with in each case 400 ml of n-hexane. After washing the organic phase with water and drying, a residue of 260 g is obtained by evaporating at 80 mbar and 40° C. Through precision distillation on an active column, 145.4 g of E-2-propyl-2-pentenoic acid is obtained therefrom corresponding to 50.4% of theory. The b.p.$_{15}$ is 135° to 136° C. The distillate solidifies to a crystalline mass with a melting point of 38° C.

EXAMPLE 3

Preparation of E-2-propyl-2-pentenoic acid from 2-hydroxy-2-propyl pentanoic acid 10 g of 2-hydroxy-2-propyl pentanoic acid, obtained in conventional manner by saponifying di-n-propyl-ketone-cyanohydrin with concentrated hydrochloric acid, and 1 g of N-methyl-pyrrolidine are heated in the oil bath to over 200° C. Splitting off of water starts at an internal temperature of 230° C. and is removed from the reaction mixture via a fitted column. The reaction at 230° to 240° C. is ended after roughly 1 hour. The residue in the reaction flask is taken up in n-hexane, washed with dilute hydrochloric acid and distilled. By precision distillation over an effective column 4.5 g of E-2-propyl-2-pentenoic acid, corresponding to 50.7% of theory are obtained. The b.p.$_{15}$ is 135° to 136° C.

EXAMPLE 4

Preparation of E-2-propyl-2-pentenoic acid sodium salt 10 g of finely ground, anhydrous sodium carbonate are refluxed for 6 hours in a solution of 142.2 g of E-2-propyl-2-pentenoic acid in 1600 ml of acetone and 54 ml of water and the solution is then filtered. After cooling to approximately −5° C., the sodium salt crystallizes from the filtrate in the form of fine, white crystals. The yield after working up the mother liquor is almost quantitative. The melting point of the crystals formed is over 300° C. The salt obtained is readily soluble in water.

I claim:

1. A process for the preparation of E-2-propyl-2-pentenoic acid of the formula:

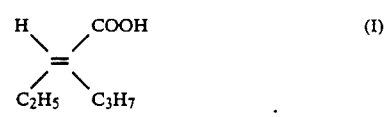 (I)

or a physiologically compatible salt thereof using -di-n-propyl-ketone-cyanohydrin of the formula:

 (II)

as the starting material, comprising the steps of:
(1) saponifying the compound of Formula II to form 2-hydroxy-2-propyl pentanoic acid of the formula:

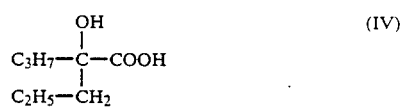 (IV)

(2) reacting the compound of formula IV at a temperature of at least 200° C. with less than a stoichiometric quantity of a tertiary amine, (3) separating the E-2-propyl-2-pentenoic acid formed in step (2) from the mixture; and, optionally (4) converting the free acid obtained in step (3) into a physiologically compatible salt thereof.

2. The process according to claim 1, in which N-methyl-pyrrolidine is used as the tertiary amine in step (2).

3. The process according to claims 1 or 2, in which the tertiary amine is used in a quantity of 5 to 10 mole %, based on the quantity of the starting compound of formula II.

4. The process according to claim 1 or 2, in which the temperature of the reaction in step (2) is 200° C. to 250° C.

5. The process according to claim 4, in which the reaction temperature is 230° C. to 240° C.

6. The process according to claim 1, in which the physiologically compatible salt of E-2-propyl-2-pentenoic acid is prepared by reacting the free acid with the corresponding salt of carbon dioxide in a mixture of acetone and water as the solvent.

7. The process according to claim 6, in which sodium carbonate is used as the carbon dioxide salt.

* * * * *